United States Patent [19]
Hubelbank

[11] Patent Number: 6,125,296
[45] Date of Patent: Sep. 26, 2000

[54] ELECTROCARDIOGRAPHIC AND OXYGEN SATURATION SIGNAL RECORDING

[75] Inventor: Mark Hubelbank, Sudbury, Mass.

[73] Assignee: Northeast Monitoring Inc., Sudbury, Mass.

[21] Appl. No.: 09/173,811

[22] Filed: Oct. 16, 1998

[51] Int. Cl.[7] .................................................. A61B 5/0404
[52] U.S. Cl. ............................................ 600/513; 600/510
[58] Field of Search ..................................... 600/513, 323, 600/510; 607/22

[56] References Cited

U.S. PATENT DOCUMENTS

| | | | |
|---|---|---|---|
| 5,343,869 | 9/1994 | Pross et al. | 600/513 |
| 5,579,775 | 12/1996 | Dempsey et al. | 600/513 |
| 5,645,068 | 7/1997 | Mezack et al. | 600/513 |

Primary Examiner—Scott M. Getzow
Attorney, Agent, or Firm—Fish & Richardson P.C.

[57] ABSTRACT

A portable machine records electrocardiographic signals and oxygen saturation signals in a removable memory device provided by an oxygen saturation sensor attached to a patient and patient lead wires with electrodes attached to the patient.

16 Claims, 2 Drawing Sheets

ELECTROCARDIOGRAPHIC AND OXYGEN SATURATION SIGNAL RECORDING

The present invention relates in general to electrocardiographic and oxygen saturation signal recording and more particularly concerns novel apparatus and technique for recording these signals on a removable memory device.

BACKGROUND OF THE INVENTION

For background on recording an electrocardiograph in digital format using a portable device reference is made to U.S. Pat. No. 4,920,489.

A typical prior art approach for measuring oxygen saturation uses a large nonportable bedside unit, or a portable unit with recording capabilities limited to oxygen saturation. These devices typically display a measurement in a hospital or laboratory setting. Such devices, when portable, are typically limited to short duration recording or recording only of oxygen saturation.

It is an important object of the invention to provide methods and means for recording a wide spectrum of electrocardiographic signal waveforms simultaneously with high resolution oxygen saturation data signals.

Another object of the invention is to achieve the preceding object while allowing the user to see both electrocardiographic and oxygen saturation data synchronized in time to facilitate a more accurate diagnosis regarding the condition of the patient.

Still another object of the invention is to achieve one or more of the preceding objects while recording all the recorded data, including the electrocardiographic and oxygen saturation data signals, on a single removable memory device to facilitate easy transfer of the recorded data to another location.

Still a further object of the invention is to achieve one or more of the preceding objects while allowing evaluation of the signal to ensure high quality recording.

Yet another object of the invention is to achieve one or more of the preceding objects while providing identification information recording in the removable memory to reduce error and facilitate tracking of data.

Still another object of the invention is to achieve one or more of the preceding objects while detecting pacemaker activity in the same recording as the oxygen saturation signal.

SUMMARY OF THE INVENTION

According to the invention, a machine for recording electrocardiographic and oxygen saturation signals on a removable memory device includes the removable memory device, an oxygen saturation sensor that provides an electrical signal representative of the oxygen saturation value of the patient, and patient lead wires with electrodes constructed and arranged to acquire electrocardiographic signals of the patient. Both the patient lead wires and the oxygen saturation sensor are coupled to the removable memory device that is constructed and arranged to store both the electrocardiographic and the oxygen saturation value signals. The machine may include amplifiers constructed and arranged to condition the electrocardiographic signals for digital conversion and an analog-digital converter constructed and arranged to convert the electrocardiograph signals into corresponding digital signals. The machine may also include a digital processor constructed and arranged to convert the electrocardiographic and oxygen saturation signals into a format suitable for storage in the removable memory device. The machine may further include circuitry constructed and arranged to record multiple single channel differential electrocardiographic signals and a 12-lead electrocardiographic signal. The machine may also include a pulse detector constructed and arranged to detect the pulse at the patient electrodes generated by a pacemaker and convert the detected pulse into a corresponding digital signal suitable for storage in the removable memory device. There may be an interface between the digital processor and the removable memory constructed and arranged to allow the use of a Personal Computer Memory Card (International Association) (PCMCIA). The interface may be constructed and arranged to allow the use of a PCMCIA which is compatible with the ATA interface standard. The machine may be constructed and arranged to store the signals in the removable memory device in an industry standard MS/DOS compatible file format. (ATA is a super set of the commands used by the IBM compatible PC AT type disk drives).

In a more specific form, there may be a multi-channel analog-to-digital converter, a digital processor constructed and arranged for both data manipulation and interaction with user-actuated signals, such as incident from a keypad and a display for interaction with the digital processor.

Numerous other features, objects and advantages of the invention will become apparent from the following detailed description when read in connection with the accompanying drawings in which:

DETAILED DESCRIPTION

Figure 1:
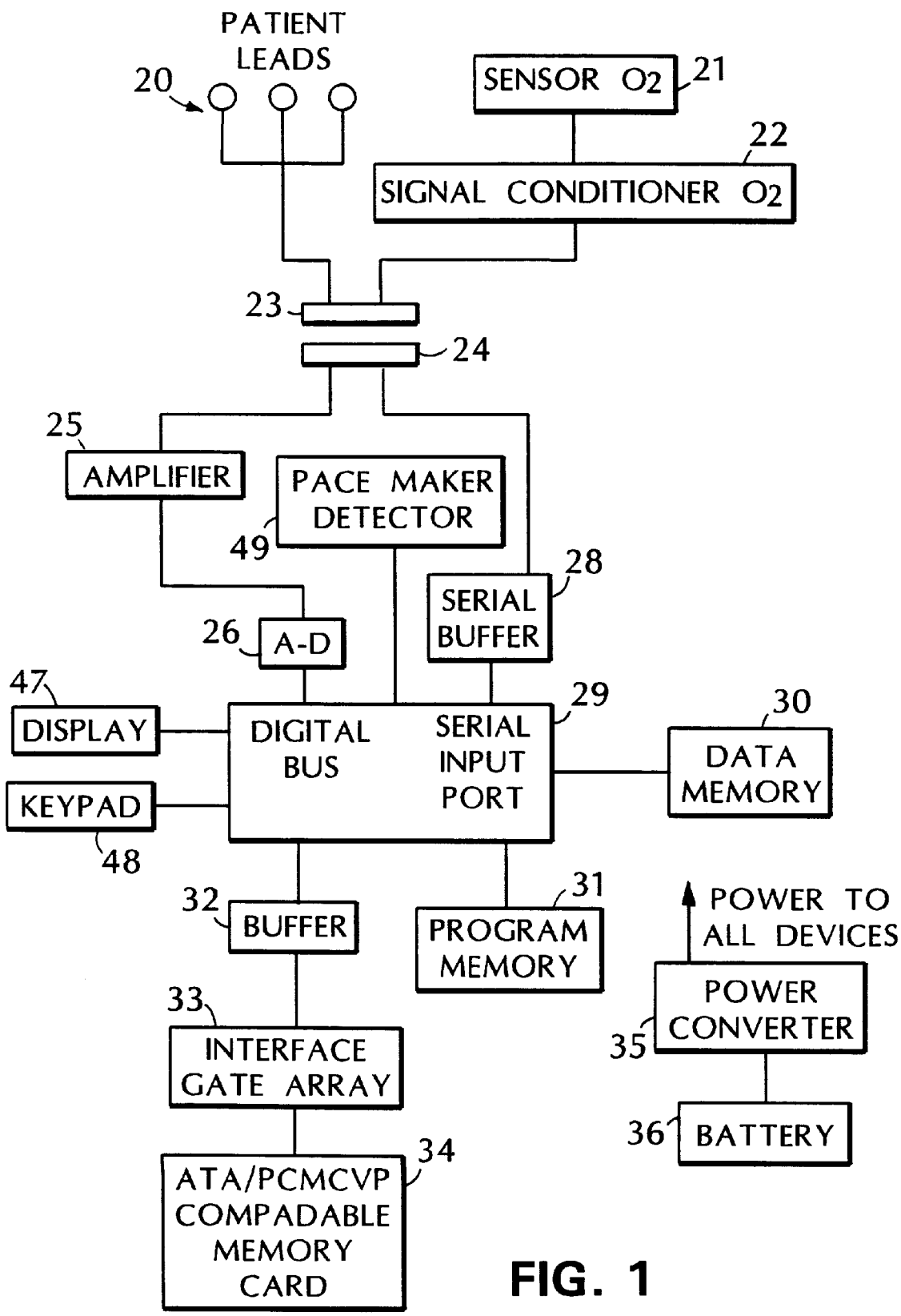
FIG. 1 is a block diagram of a system according to the invention.

With reference now to the drawings and more particularly FIG. 1 thereof, there is shown a block diagram illustrating the logical arrangement of a system according to the invention. Oxygen sensor 21, typically attached to a patient finger or other suitable part of the body, provides a signal representative of oxygen saturation to signal conditioner 22 that provides a signal through connector 40 in digital form representative of patient oxygen saturation. Patient leads 20 are connected to electrodes attached to the patient's skin to a male connector 23 that also receives the oxygen saturation digital signal from signal conditioner 22 and is connected to female connector 24. The location and number of electrodes depends on the clinical requirements. The machine is constructed and arranged to allow processing of signals from a minimum of three electrodes typically used for recording a single differential electrocardiographic signal with a reference electrode up to full medical 12-lead set which requires nine signal electrodes and a reference electrode.

Signal conditioner 22 typically provides at least three measurement signals per second; however, the machine may function with a wide variety of measurement signal rates.

Figure 3:
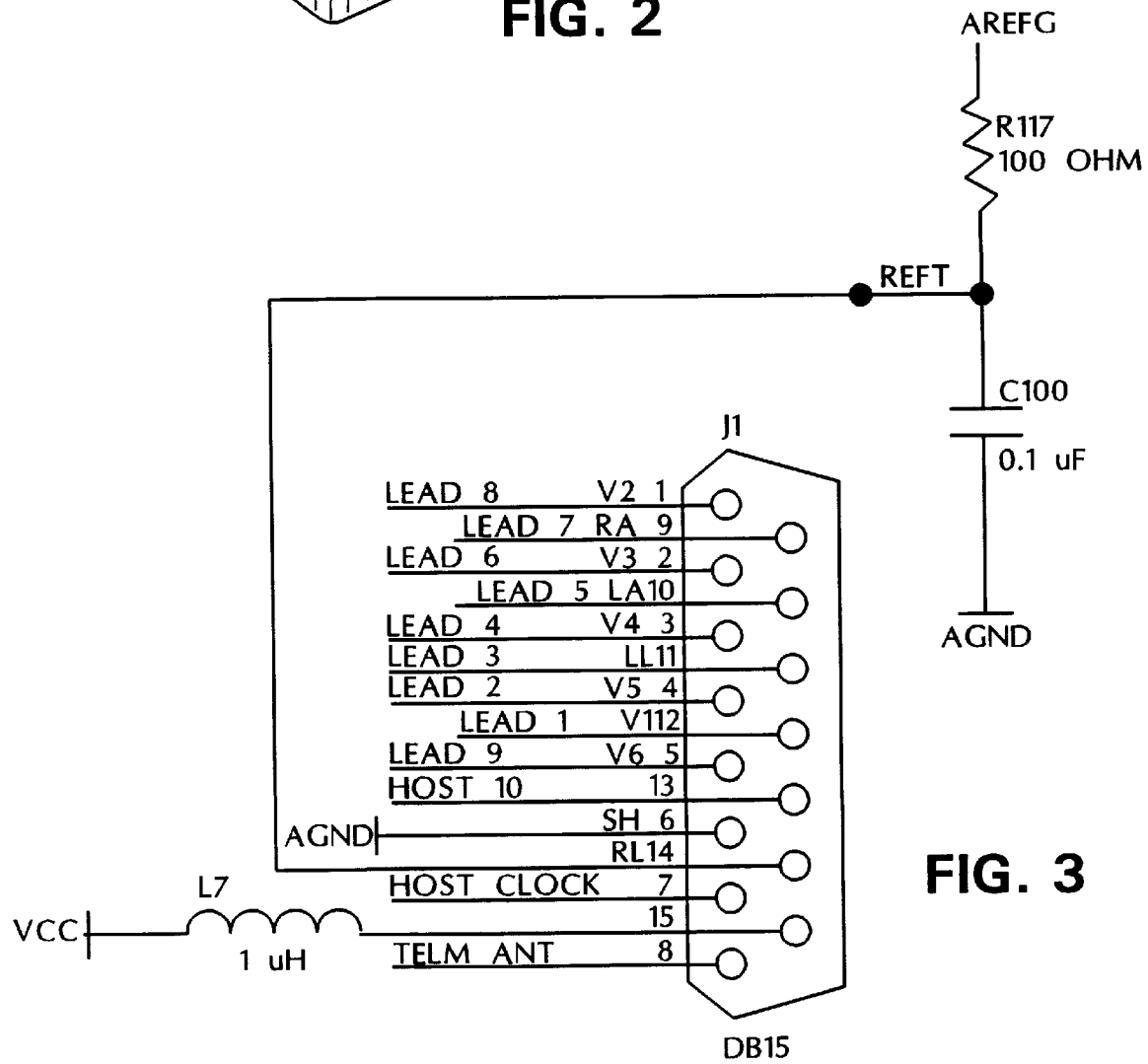
FIG. 3 illustrates an interface according to the invention which provides compatibility with patient cables commonly used in hospitals.

Female connector 24 is in the recorder and typically is a DB15 female connector wired using the connections shown in FIG. 3. This arrangement is consistent with commonly used industry standard patient cables which do not use pins 13 and 15 and will function correctly with the machine although they will not provide oxygen saturation signals.

The electrocardiograph signals from patient wires 20 energize amplifier 25. Amplifier 25 increases the magnitude of the signals from typical maximum values of 1.2 millivolts to a maximum value of 1.5 volts. Analog-to-digital converter 26 then converts the resulting voltage to a digital representation. Typically there is an amplifier for each electrocardiographical signal and at least one multi-channel analog-to-digital converter for each electrocardiographical signal.

Serial buffer 28 receives the series digital signal from signal conditioner 22 representative of oxygen saturation and converts this signal to parallel form.

When the patient has a pacemaker, pacemaker detector 49 detects the pacemaker pulse in the signal which has been amplified by amplifier 25 and converts the detected pacemaker pulse into a digital representation delivered to processor 29.

Processor 29 receives electrocardiographic digital signals from the digital-to-analog converter 26, digital pacemaker pulse signals from pacemaker detector 49 and digital oxygen saturation signals from serial buffer 28. Data memory 30 buffers these digital data signals, and processor 29 converts them to a format that can be stored in removable memory 34. This format is typically, but not necessarily, a MS/DOS compatible format. Program memory 31 typically stores a program for converting these digital signals into the MS/DOS compatible format. Digital signal processor 29, data memory 30 and program memory 31 may be on a single chip or on separate chips. Buffer 32 receives the converted digital data signals in MS/DOS form and delivers these signals to interface gate array 33 that may perform the optional function of simulating an industry standard ATA/PCMCIA interface so that removable memory device 34 may be used.

Digital processor 29 controls display 47 to typically display a set of numbers indicating the impedance of the patient electrodes, which is a measure of the quality of the electrodes, and the quality of the oxygen saturation measurement signals during the initial setup of the device. Once recording has begun, display 47 may optionally show the oxygen saturation value, and/or any other data useful to the procedure.

Keypad 48 allows the user to enter data and for user interaction. This data may include, but is not limited to, supplying a patient identification to be recorded on the removable memory, specifying operating mode and entering patient diary entries.

Battery 36 furnishes energy to power converter 35 that provides the voltages required by the various components of the system. Battery 36 may be replaced by an alternate energy source.

Figure 2:
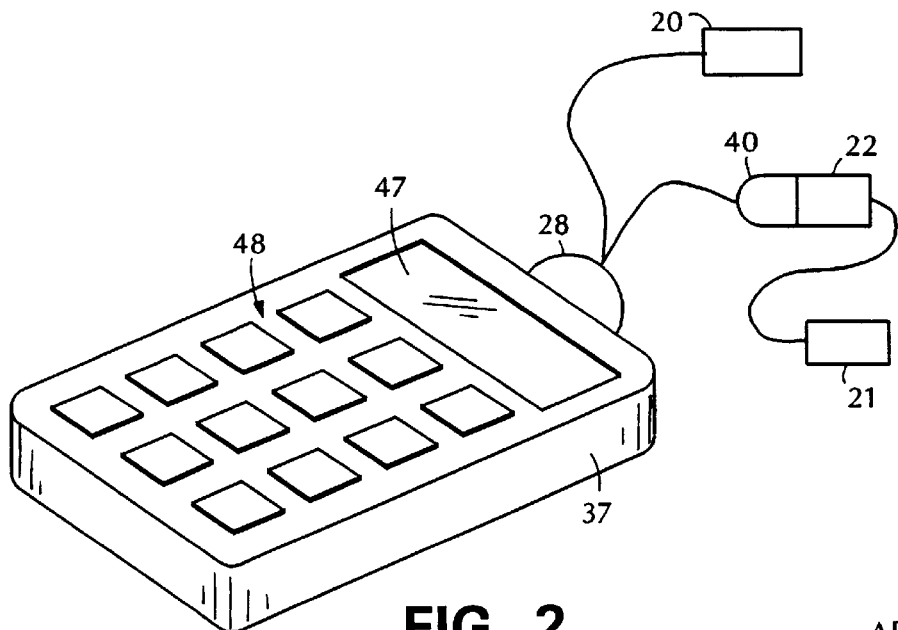
FIG. 2 is a pictorial representation of a portable device incorporating the elements of FIG. 1.

Referring to FIG. 2, there is shown a pictorial representation of an embodiment of the invention. The same reference symbols identify corresponding elements throughout the drawings. Portable recording device 37 has a front panel with keypad 48 and display 47.

There has been described novel apparatus and techniques for portably recording in a detachable memory device digital signals representative of electrocardiographic signals and oxygen saturation signals simultaneously. It is evident that those skilled in the art may now make numerous uses and modifications of and departures from the specific apparatus and techniques herein disclosed without departing from the inventive concepts. Consequently, the invention is to be construed as embracing each and every novel feature and novel combination of features present in or possessed by the apparatus and techniques herein disclosed.

What is claimed is:

1. A portable machine for recording electrocardiographic signals and oxygen saturation signals on a removable memory device comprising, an oxygen saturation sensor constructed and arranged for attachment to a patient to provide an oxygen saturation value electrical signal representative of the oxygen saturation value of the patient, patient lead wires with electrodes constructed and arranged to attach to the skin of said patient to furnish electrocardiographic signals, a removable memory device coupled to said patient lead wires and said oxygen saturation sensor constructed and arranged to store the electrocardiographic signals and the oxygen saturation value signals, and a pacemaker detector constructed and arranged to detect the pacemaker pulses at the electrodes generated by a pacemaker when the patient has a pacemaker and convert the detected pacemaker pulses into a digital format suitable for storage in the removable memory device and coupled to the removable memory device and the patient electrodes when the patient has a pacemaker.

2. A portable machine in accordance with claim 1 and further comprising, amplifiers coupled to said patient lead wires and constructed and arranged to amplify electrocardiographic signals on said patient lead wires for digital conversion, and an analog-to-digital converter coupled to said amplifiers constructed and arranged to convert the electrocardiographic signals into corresponding digital signals.

3. A portable machine in accordance with claim 2 and further comprising, a digital processor constructed and arranged to convert the electrocardiographic signals and oxygen saturation signals into signals of a format suitable for storage in the removable memory device and coupled to the removable memory device, the analog-to-digital converter and the oxygen saturation sensor.

4. A portable machine in accordance with claim 3 wherein the machine is constructed and arranged to record multiple single channel differential electrocardiographic signals and a 12-lead electrocardiographic signal.

5. A portable machine in accordance with claim 3 and further comprising, an interface between the digital processor and the removable memory device constructed and arranged to allow the removable memory device to comprise a PCMCIA memory card.

6. A portable machine in accordance with claim 3 and further comprising an interface between the digital processor and the removable memory device constructed and arranged to allow the removable memory device to comprise a PCMCIA memory card compatible with the ATA interface standard.

7. A portable machine in accordance with claim 3 constructed and arranged to store the digital data signals in an industry standard MS/DOS compatible file format.

8. A portable machine in accordance with claim 3 wherein said analog-to-digital converter is a multi-channel analog-to-digital converter, and further comprising, a display for interaction with the digital processor, and a keypad for data entry coupled to the digital processor.

9. A portable machine in accordance with claim 8 wherein the removable memory device is constructed and arranged to record multiple single channel differential electrocardiographic signals and a 12-lead electrocardiographic signal.

10. A portable machine in accordance with claim 9 and further comprising an interface between the digital processor and the removable memory device constructed and arranged to allow the removable memory device to comprise a PCMCIA memory card.

11. A portable machine in accordance with claim 10 wherein the interface is constructed and arranged to allow the use of the PCMCIA memory card that is compatible with the ATA interface standard.

12. A portable machine in accordance with claim 11 wherein the interface is constructed and arranged to allow storing the digital data signals in the removable memory device in an industry standard MS/DOS compatible file format.

13. A portable machine in accordance with claim 8 wherein the digital processor is constructed and arranged to furnish signals to the display representative of the condition of the oxygen saturation sensor and its signal quality, said display then displaying the condition of the oxygen saturation sensor and its signal quality.

14. A portable machine in accordance with claim 8 wherein said digital processor is constructed and arranged to accept patient identification signals from said keypad and to furnish oxygen saturation value signals to the display during recording.

15. A portable machine in accordance with claim 8 and further comprising a connector constructed and arranged to allow connection of the oxygen saturation signals and patient wires so as to make the patient cable comprising the patient wires compatible with industry standard patient cables.

16. A method of recording oxygen saturation signals and electrocardiographic signals in the removable memory device of the portable machine of claim 1 comprising, attaching said electrodes to the skin of a patient to acquire said electrocardiographic signals and said pacemaker pulses, attaching said oxygen saturation sensor to said patient to provide said oxygen saturation value electrical signals, and converting the electrocardiographic signals, oxygen saturation value electrical signals and pacemaker pulses into corresponding digital signals, and storing said corresponding digital signals in said removable memory device.

\* \* \* \* \*